(12) United States Patent
Julien et al.

(10) Patent No.: US 12,352,744 B2
(45) Date of Patent: Jul. 8, 2025

(54) METHOD AND PORTABLE READER FOR ANALYZING A BIOLOGICAL FLUID SPECIMEN

(71) Applicant: IKI, Carbonne (FR)

(72) Inventors: Guillaume Julien, Muret (FR); Morgane Leblanc, Toulouse (FR); Bernard Bouissou, Cugnaux (FR); Didier Fabbro, Carbonne (FR); Julien Calve, Plaisance du Touch (FR); Philippe Lumbierres, Carbonne (FR); Cyril Cauchois, Saint Julien sur Garonne (FR); Jean-Christophe Cau, Toulouse (FR)

(73) Assignee: IKI, Carbonne (FR)

( * ) Notice: Subject to any disclaimer, the term of this patent is extended or adjusted under 35 U.S.C. 154(b) by 777 days.

(21) Appl. No.: 17/637,066

(22) PCT Filed: Sep. 16, 2020

(86) PCT No.: PCT/EP2020/075811
§ 371 (c)(1),
(2) Date: Feb. 21, 2022

(87) PCT Pub. No.: WO2021/052983
PCT Pub. Date: Mar. 25, 2021

(65) Prior Publication Data
US 2022/0299501 A1  Sep. 22, 2022

(30) Foreign Application Priority Data
Sep. 17, 2019  (FR) ...................................... 1910244

(51) Int. Cl.
*G01N 33/52* (2006.01)
*B01L 3/00* (2006.01)
*G01N 21/78* (2006.01)

(52) U.S. Cl.
CPC .......... *G01N 33/521* (2013.01); *B01L 3/5023* (2013.01); *G01N 21/78* (2013.01);
(Continued)

(58) Field of Classification Search
None
See application file for complete search history.

(56) References Cited

U.S. PATENT DOCUMENTS

| | | |
|---|---|---|
| 5,281,395 A | 1/1994 | Markart et al. |
| 5,611,995 A | 3/1997 | De Zoeten et al. |

(Continued)

FOREIGN PATENT DOCUMENTS

| | | |
|---|---|---|
| EP | 2975408 A1 | 1/2016 |
| EP | 3499220 A1 | 6/2019 |
| WO | 9726083 A1 | 7/1997 |

*Primary Examiner* — Lore R Jarrett
(74) *Attorney, Agent, or Firm* — H&I PARTNERS; Chai Im; C. Andrew Im

(57) ABSTRACT

A method for analyzing a biological fluid specimen. The collection cartridge is inserted into a reader. The plurality of reactive elements of the collection cartridge following insertion of the collection cartridge is optically read recurrently. The first color change of at least one reactive element of the collection cartridge is detected and dated following the recurrent optical reading. The biological fluid specimen from the collection cartridge is analyzed following the detection of the color change of at least one reactive element of the collection cartridge.

6 Claims, 14 Drawing Sheets

(52) U.S. Cl.
CPC ... *B01L 2200/04* (2013.01); *B01L 2300/0609* (2013.01); *B01L 2300/0654* (2013.01)

(56) References Cited

U.S. PATENT DOCUMENTS

| | | |
|---|---|---|
| 6,867,051 B1 | 3/2005 | Anderson et al. |
| 2012/0300211 A1 | 11/2012 | Wang |
| 2014/0273187 A1* | 9/2014 | Johnson .............. G01N 27/3272 435/287.2 |
| 2014/0286550 A1* | 9/2014 | Beule ................. G01N 21/8483 382/128 |
| 2016/0011188 A1* | 1/2016 | Anderberg ........... G01N 33/525 264/250 |
| 2016/0103075 A1 | 4/2016 | Borich et al. |
| 2016/0187333 A1* | 6/2016 | Moll ................. B01L 3/502715 506/18 |
| 2016/0370366 A1 | 12/2016 | Fleming et al. |
| 2017/0014822 A1* | 1/2017 | Ker .................... G01N 27/3272 |
| 2019/0086434 A1* | 3/2019 | Aoki ................. G01N 35/1016 |

* cited by examiner

METHOD AND PORTABLE READER FOR ANALYZING A BIOLOGICAL FLUID SPECIMEN

RELATED APPLICATIONS

This application is a § 371 application of PCT/EP2020/075811 filed Sep. 16, 2020, which claims priority from French Patent Application No. 1910244 filed Sep. 17, 2019, each of which is incorporated herein by reference in its entirety.

TECHNICAL FIELD OF THE INVENTION

The present invention relates to a portable reader for analyzing a biological liquid sample and a method for analyzing a biological liquid sample. It applies, in particular, to a system for analyzing a biological liquid sample comprising a cartridge for collecting the biological liquid sample inserted in the portable reader.

BACKGROUND OF THE INVENTION

It is common, among health professionals, to be able to analyze a biological liquid sample such as urine or else saliva. It is known to use strips equipped with a few reactive elements whose color may vary in contact with the biological liquid after soaking the strip in the biological liquid. The interpretation of the color change can be performed either with the naked eye according to an analysis table allowing correlating the colors with a concentration of compound in the biological liquid, or by inserting the strip into a bulky reading apparatus allowing analyzing the strip.

It has already been attempted to overcome this problem by offering the general public to themselves soak strips equipped with reactive elements in a jar comprising for example urine, and to themselves analyze with the naked eye, the color change of the reagents and interpret the colors according to the instructions provided with the strip.

This home solution does not always reliably inform the user, the user may have difficulty discerning a color change relative to the instructions, the time of soaking of the strip in the biological liquid not being necessarily mastered by the user, the latency time between the end of soaking and the interpretation of the colors of the reagents also not always being mastered by the user.

OBJECT AND SUMMARY OF THE INVENTION

The present invention aims at overcoming these drawbacks with a completely innovative approach.

To this end, according to a first aspect, the present invention relates to a portable reader for analyzing a biological liquid sample intended to receive a cartridge for collecting the biological liquid sample, the reader comprising a reader housing extending along a longitudinal axis between two lateral ends, the reader housing comprising a lateral access opening intended for an insertion or an extraction of the collection cartridge along the longitudinal axis; a lower portion comprising a reader housing bottom; a reader cover intended for closing the reader housing; an electronic card with printed circuit arranged in the reader housing bottom; a plurality of optical transmitter-receiver assemblies arranged on the upper face of the electronic card with printed circuit, the optical transmitter-receiver assemblies of the plurality of assemblies being arranged one after the other along the longitudinal axis; a cartridge support element, extending longitudinally, comprising a cartridge support bottom which is extending longitudinally, and arranged facing and distant from the upper face of the electronic card with printed circuit; each optical transmitter-receiver assembly being arranged facing an opening of the cartridge support bottom; an electronic monitoring unit electrically connected to the plurality of optical transmitter-receiver assemblies; the electronic monitoring unit being configured to control each optical transmitter-receiver assembly in a mode of emitting light and receiving the reflected light so as to be able to perform an optical reading for the purpose of analyzing a biological liquid.

The invention is implemented according to the embodiments and the variants exposed below, which are to be considered individually or according to any technically operative combination.

Advantageously, the cartridge support element can comprise two lateral walls extending longitudinally from the lateral access opening and arranged on either side of the support bottom forming a guide for inserting the collection cartridge.

According to a second aspect, the present invention relates to a system for analyzing a biological liquid sample comprising the reader; a cartridge for collecting the biological liquid sample configured to be arranged to bear on the cartridge support bottom of the reader, the cartridge comprising a cartridge housing extending longitudinally between two lateral ends, and comprising a cartridge housing bottom; a plurality of color-changing reactive elements arranged one after the other along the longitudinal axis; each reactive element being arranged in the cartridge housing bottom and facing an opening of the cartridge housing bottom; the electronic monitoring unit configured to analyze a biological liquid sample by detecting a color change of each reactive element following an optical reading.

The invention is implemented according to the embodiments and the variants exposed below, which are to be considered individually or according to any technically operative combination.

Advantageously, the system can comprise a position sensor arranged in the reader housing and electrically connected to the monitoring unit, the position sensor may be configured to detect that each reactive element of the cartridge is arranged facing an optical transmitter-receiver assembly of the reader; and to send a control signal, to the electronic monitoring unit, for optical reading of each reactive element in a recurrent manner following the detection of the arrangement facing each reactive element with an optical transmitter-receiver assembly.

Advantageously, the cartridge may comprise a biological liquid diffusion band, extending longitudinally, arranged in the cartridge housing over the top of the plurality of reactive elements; the diffusion band being configured to be in direct contact with each reactive element of the plurality of reactive elements; the cartridge may also comprise a flexible portion of the cartridge housing bottom arranged opposite each reactive element of the plurality of reactive elements and a cartridge cover arranged over the top of the diffusion band. The system may comprise at least one pushing element cooperating with the cartridge cover and configured to push the cartridge in the direction of the cartridge support bottom and crush the flexible portion of the cartridge housing bottom against a protruding portion of the cartridge support bottom when inserting the cartridge into the reader such that each reactive element is in contact with the diffusion band.

Advantageously, the collection cartridge may comprise a stop arranged on the outer portion of the collection cartridge housing and configured to abut against the reader housing when inserting the collection cartridge into the reader and stop the insertion of the cartridge into the reader; the cartridge may also comprise an absorbent reservoir band extending longitudinally and configured for the deposition of biological liquid; the absorbent reservoir band being held in a movable support arranged at least partially in the collection cartridge, the movable support being configured to guide the absorbent reservoir band in contact with the diffusion band after a stop insertion of the collection cartridge into the reader; the cartridge may also comprise a handle arranged outside the cartridge housing and in mechanical connection with the movable support, the handle being configured to push the absorbent reservoir band in direct contact with the diffusion band following the stop insertion of the cartridge into the reader.

According to a third aspect, the present invention relates to a method for analyzing a biological liquid sample, the method being implemented by the system for analyzing a biological liquid sample; the method comprising steps of: inserting the collection cartridge into the reader; recurrent optical reading of the plurality of reactive elements of the cartridge following the insertion of the cartridge; detecting a first color change of at least one reactive element of the plurality of reactive elements following the recurrent optical reading step; dating the first detected color change; analyzing the biological liquid sample from the cartridge following the detection of a color change of at least one reactive element of the cartridge.

The invention is implemented according to the embodiments and the variants exposed below, which are to be considered individually or according to any technically operative combination.

Advantageously, the reader of the system can comprise a position sensor arranged in the reader housing, the method may comprise steps prior to the recurrent optical reading step, of: detecting by the position sensor of the arrangement of each reactive element of the cartridge facing an optical transmitter-receiver assembly of the reader; and authorizing the recurrent optical reading step on condition of the detection of the arrangement of each reactive element of the cartridge facing an optical transmitter-receiver assembly of the reader.

Advantageously, the cartridge may comprise a biological liquid diffusion band arranged over the top of the plurality of reactive elements, the method may comprise a step of direct contacting of the diffusion band on the plurality of reactive elements following the step of inserting the cartridge into the reader by crushing the cartridge by the reader.

Advantageously, the cartridge may comprise an absorbent reservoir band configured for the deposition of biological liquid, the method may comprise a step of direct contacting of a portion of the absorbent reservoir band on the diffusion band by longitudinal pushing of the collection cartridge when it is inserted into the reader.

BRIEF DESCRIPTION OF THE FIGURES

Other advantages, aims and features of the present invention emerge from the following description made, for the purpose of explanation and without limitation, with reference to the appended drawings, in which.

DESCRIPTION OF THE EMBODIMENTS

Figure 1:
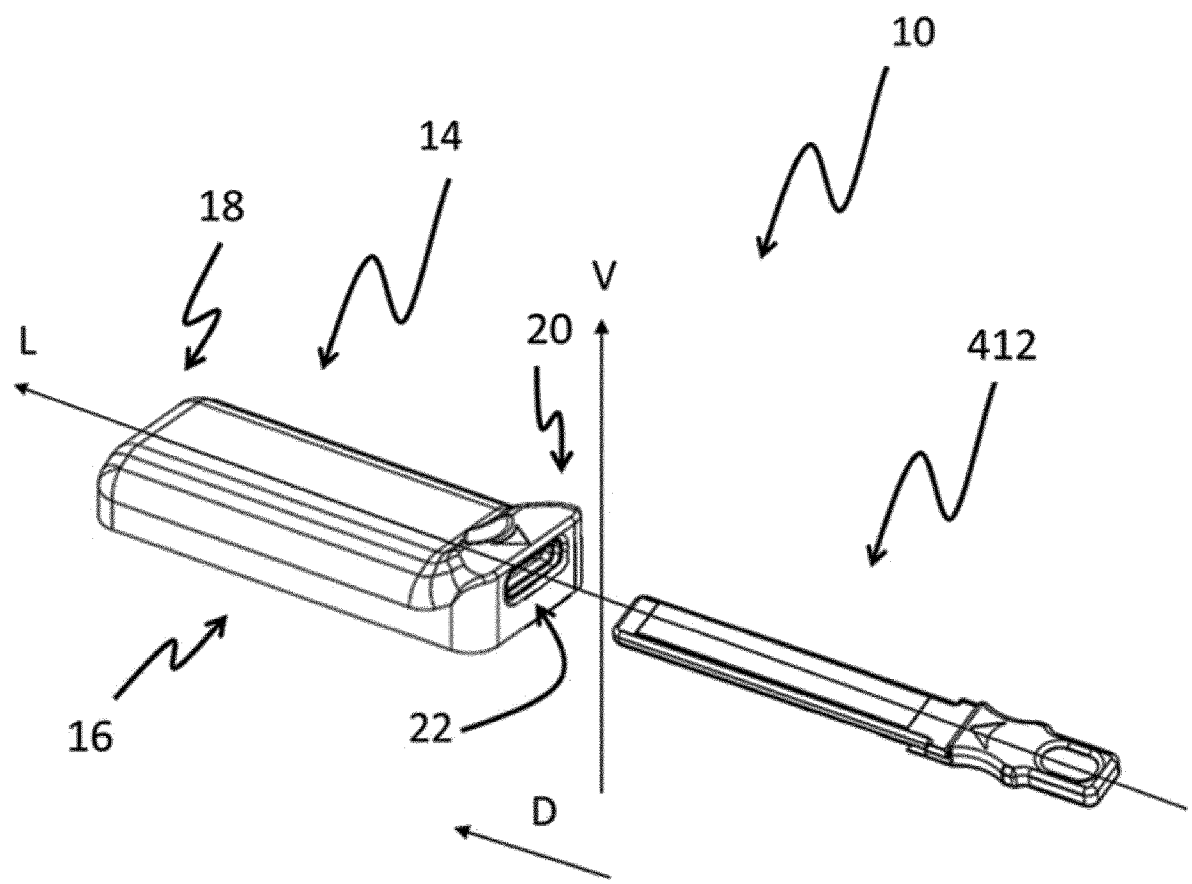
FIG. 1 is a perspective schematic view of a first embodiment of a system for analyzing a biological liquid sample comprising a cartridge for collecting the biological liquid sample and a reader for analyzing the biological liquid sample.

According to FIG. 1, a system 10 for analyzing a biological liquid sample comprises a device, or cartridge 412 for collecting a biological liquid sample, and a portable reader 14 for analyzing a biological liquid sample. For the purposes of positioning the elements with each other, and without limitation with regard to the overall orientation of the collection cartridge 412 and the reader 14, left and right orientations are defined along a longitudinal axis L and top and bottom, or upper and lower orientations are defined along a vertical axis V. The cartridge 412 for collecting the biological liquid sample is intended to be inserted into the portable reader 14 for analyzing the biological liquid. The reader 14 comprises a housing 16 of the reader 14 extending generally along the longitudinal axis L between two left and right lateral ends 18, 20. The housing 16 of the reader 14 comprises a lateral access opening 22 intended for an insertion in a longitudinal direction D or for an extraction of the collection cartridge 412.

Figure 2:
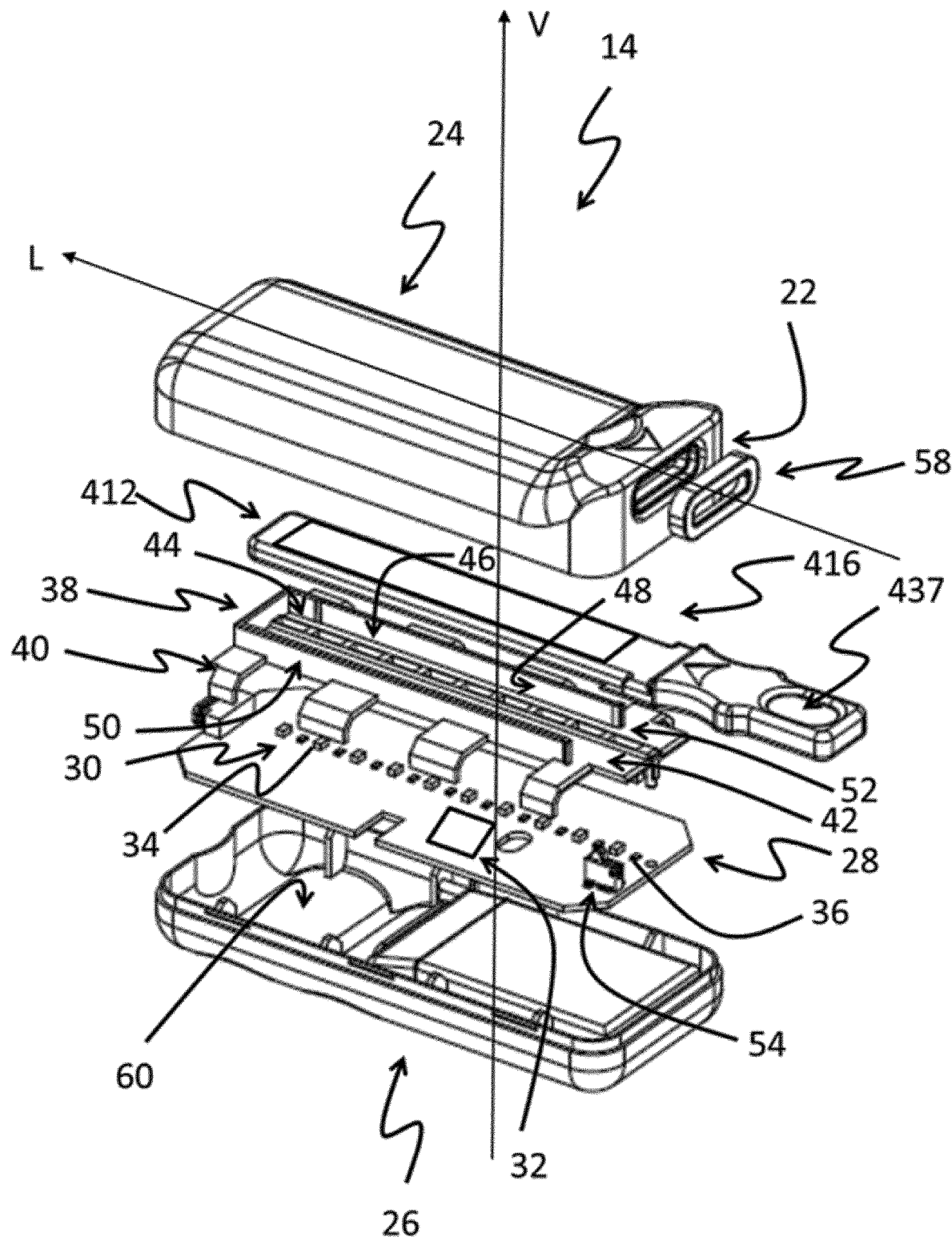
FIG. 2 is a schematic perspective exploded top view of the analysis reader comprising the cartridge for collecting the biological liquid sample according to the first embodiment.

According to FIG. 2 and according to a first embodiment, the reader 14 of FIG. 1 comprises the housing 16 of the reader 14 comprising a housing bottom 26 of the reader 14 and a cover 24 of the reader 14 intended to close the housing 16 of the reader 14. The reader 14 also comprises an electronic card 28 with printed circuit arranged in the housing bottom 26 of the reader 14. The upper face of the electronic card 28 with printed circuit comprises a plurality of optical transmitter-receiver assemblies 30, the optical transmitter-receiver assemblies 30 of the plurality of assemblies 30 being arranged one after the other along the longitudinal axis L.

The reader 14 comprises an electronic monitoring unit 32, advantageously arranged on the electronic card 28 with printed circuit, and electrically connected to the plurality of optical transmitter-receiver assemblies 30. The electronic monitoring unit 32 is configured to control each optical transmitter-receiver assembly 30 in a mode of emitting light and receiving the reflected light so as to be able to perform an optical reading for the purpose of analyzing a biological liquid.

More particularly, each optical transmitter-receiver assembly 30 comprises a light source 34, preferably white light source, and an optical sensor 36, preferably of the image sensor type, such that the electronic monitoring unit 32 can perform a color analysis of color-changing reactive elements in contact with biological liquid.

By way of non-limiting example, the image sensor can be a sensor of the red, green and blue sensor type, so that the color information communicated to the electronic monitoring unit by the sensor is information relating to the ratio of each primary color detected by the sensor. The choice of the sensor, more particularly its spectral range, is dictated by the spectral ranges of the color changes coming from the reagents.

In the context of the invention, the term "color change" should mean the evolution of the color of a reactive element when it is brought into contact with a biological liquid, for example and without limitation, of a change in the color from orange to blue for an indication of acidity (or else denoted 'pH') of biological liquid, but also of an appearance of color, that is to say from the white aspect of a reactive element to a pink coloration when detecting nitrites in a biological liquid in contact with the appropriate reactive element.

The reader 14 also comprises a cartridge support element 38 extending along the longitudinal axis L and comprising fastening means 40 allowing it to be fastened in the housing 16, preferably in a secured manner with the electronic card 28 with printed circuit. More particularly, the cartridge support element 38 comprises a cartridge support bottom 42 extending longitudinally, and arranged facing and distant from the upper face of the electronic card 28 with printed circuit. According to this first embodiment, the cartridge support bottom 42 comprises a plurality of openings 44, 46 of the support bottom 42, each optical transmitter-receiver assembly 30 being arranged facing an opening 44 of the cartridge support bottom 42. In particular, each light source 34 of an optical transmitter-receiver assembly 30 is separated from the optical sensor 36 of the same optical transmitter-receiver assembly 30 by a vertical wall allowing suppressing the spectral reflections.

Figure 3:
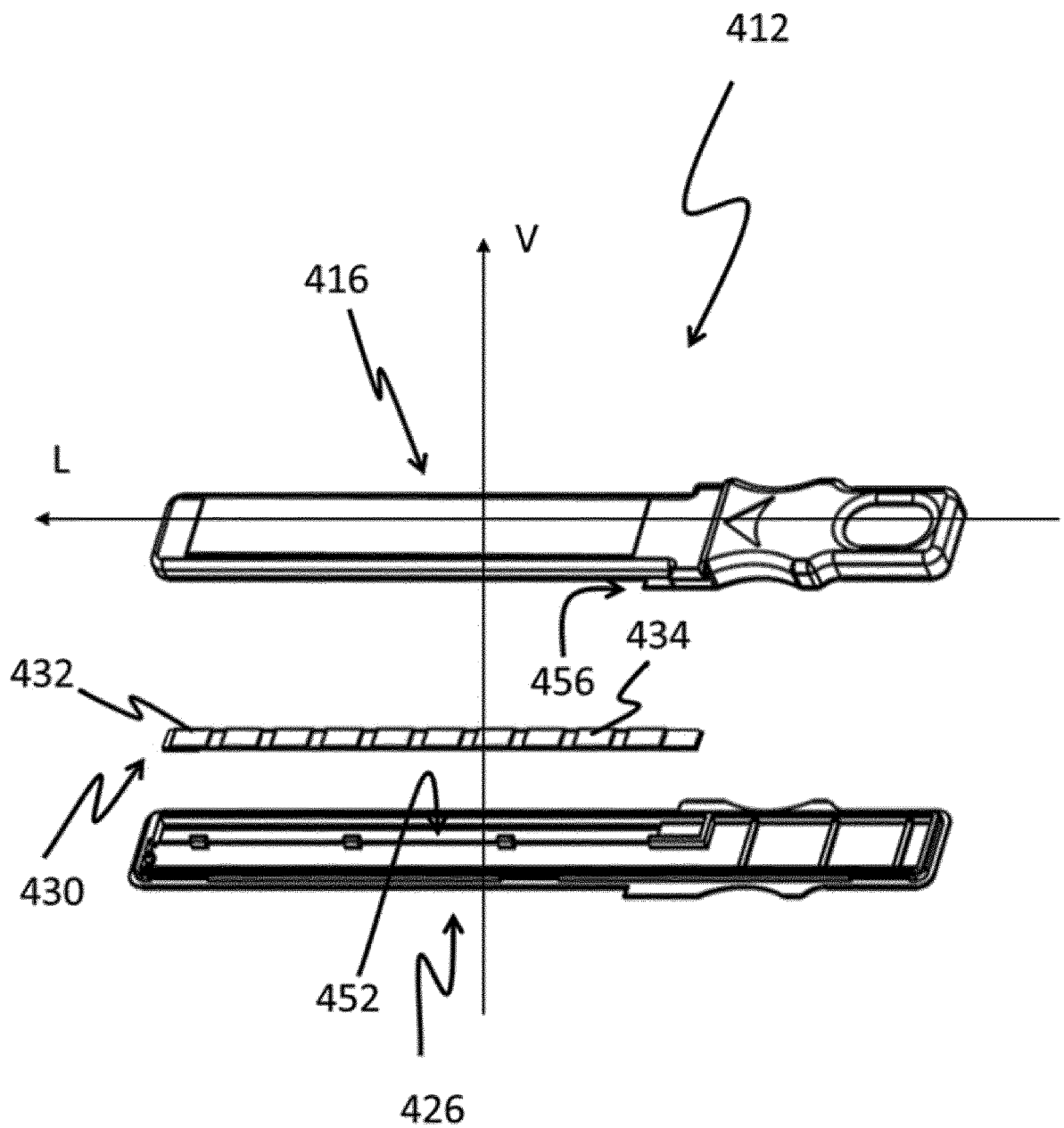
FIG. 3 is a perspective exploded schematic top view of the cartridge for collecting the biological liquid sample according to the first embodiment.

To this end, according to FIG. 2 and FIG. 3, and according to the first embodiment of the reader 14, the system 10 for analyzing a biological liquid sample comprises the cartridge 412 for collecting the biological liquid sample of FIG. 1, the collection cartridge 412 being configured to bear on the cartridge support bottom 42 of the reader 14. The collection cartridge 412 comprises a cartridge housing 416 extending longitudinally and comprising a cartridge housing bottom 426. The collection cartridge 412 comprises a plurality of color-changing reactive elements 432, 434 arranged one after the other along the longitudinal axis L, each reactive element 432, 434 being arranged in the cartridge housing bottom 426 and facing an opening 452 of the cartridge housing bottom 426. Optionally, the plurality of reactive elements 432, 434 can be arranged on a strip 430, preferably a self-adhesive and transparent or translucent strip.

In the presence of the collection cartridge 12, the electronic monitoring unit 32 is configured to monitor a recurring control of a mode of emitting light and receiving the reflected light from each optical transmitter-receiver assembly 30. The electronic monitoring unit 32 is configured to analyze a biological liquid sample by detecting a color change of each reactive element 432, 434 following an optical reading of the color of each reactive element 432, 434.

According to FIG. 2, in order to ensure a reliable optical reading by the reader 14 of the color change of the reactive elements 432, 434 of the collection cartridge, the system 10 comprises a position sensor 54 arranged in the housing 16 of the reader 14. The position sensor 54 is electrically connected to the monitoring unit 32. The position sensor 54 is configured to detect that each reactive element 432, 434 of the cartridge is arranged facing an optical transmitter-receiver assembly 30 of the reader 14. When the position sensor 54 finds that each reactive element 432, 434 of the cartridge is arranged facing an optical transmitter-receiver assembly 30 of the reader 14, the position sensor 54 is configured to send a control signal to the electronic monitoring unit 32 authorizing the control unit to perform an optical reading of each reactive element 432, 434 in a recurring manner.

More particularly, according to FIG. 2, the position sensor 54 comprises a switch arranged on the electronic card 28 with printed circuit, and configured to cooperate with a position stop 456 of the collection cartridge 412. In other words, the collection cartridge 412 comprises a position stop 456 configured to hit and trigger a switch arranged in the reader 14 when the collection cartridge 412 is correctly positioned in the reader 14, that is to say when each reactive element 432, 434 arranged in the collection cartridge 412 is arranged facing an optical transmitter-receiver assembly 30 through the plurality of openings 44, 46 of the cartridge support bottom 42 of the reader 14 and the opening 452 of the cartridge support bottom 426.

In particular, and according to FIG. 3, the position stop 456 comprises a lug arranged protruding on a lateral rim of the cartridge housing 416. The position along the longitudinal axis L of the position stop 456 on the lateral rim of the cartridge housing 416 and the position along the longitudinal axis L of the switch should be calibrated such that when the position stop 456 hits the switch, each reactive element 432, 434 of the cartridge is arranged facing an optical transmitter-receiver assembly 30 of the reader 14. The position stop 456 on the lateral rim of the cartridge housing 416, or lug, is preferably arranged in the vicinity of the right end of the collection cartridge so as not to bring any constraints on the length along the longitudinal axis L, of the collection cartridge 412.

It should be noted, by way of non-limiting examples, that alternatively, the position sensor 54 may comprise an infrared barrier arranged transversely on the cartridge support element 38, preferably at the end of the cartridge support element 38 opposite the lateral access opening 22 of the housing 16 of the reader 14, such that the infrared barrier can be cut by the left end of the cartridge housing 416 during its insertion into the reader 14. Alternatively, the position sensor 54 may comprise a push button-type switch also arranged at the end of the cartridge support element 38, this switch being able to be activated by crushing the left end of the cartridge housing 416 on the push button when it is inserted into the reader 14.

According to FIG. 2, in order to facilitate the insertion of the collection cartridge 412 into the reader 14, the cartridge support element 38 comprises two lateral walls 48, 50 arranged oppositely on either side of the support bottom 42 cartridge, each lateral wall 48, 50 extending longitudinally from the lateral access opening 22. The arrangement of the lateral walls 48, 50 on either side of the cartridge support bottom 42 forms a collection cartridge insertion guide 52.

According to FIG. 2, the reader 14 is configured to be used as a support for the collection cartridge 412 when depositing biological liquid allowing imbibing the reactive elements 432, 434. To this end, the collection cartridge 412 should comprise a deposit portion 437 of biological liquid accessible from outside the reader 14 when the collection cartridge 412 is inserted into the reader 14. According to this embodiment, the reader 14 comprises a seal 58 arranged in the lateral access opening 22 of the reader 14 so as to ensure a sealing of the lateral opening 22 for accessing any biological liquid which can be deposited on the collection cartridge 412 after its insertion into the reader 14. The seal 58 is configured to come into compression around the portion of the collection cartridge 412 arranged through the lateral access opening 22 when the collection cartridge 412 is correctly positioned in the reader 14.

In order to facilitate the handling of the reader, in particular during the deposition of biological liquid on the liquid deposition portion 437 of the collection cartridge 412 inserted into the reader 14, the housing bottom 26 of the reader 14 comprises, on the lower face thereof, a gripping means 60 for manual gripping of the reader 14, the gripping means 60 particularly comprising at least one surface forming a domed hollow towards the inside of the housing 16 the reader 14 and extending longitudinally in an arch-type shape.

Figure 4:
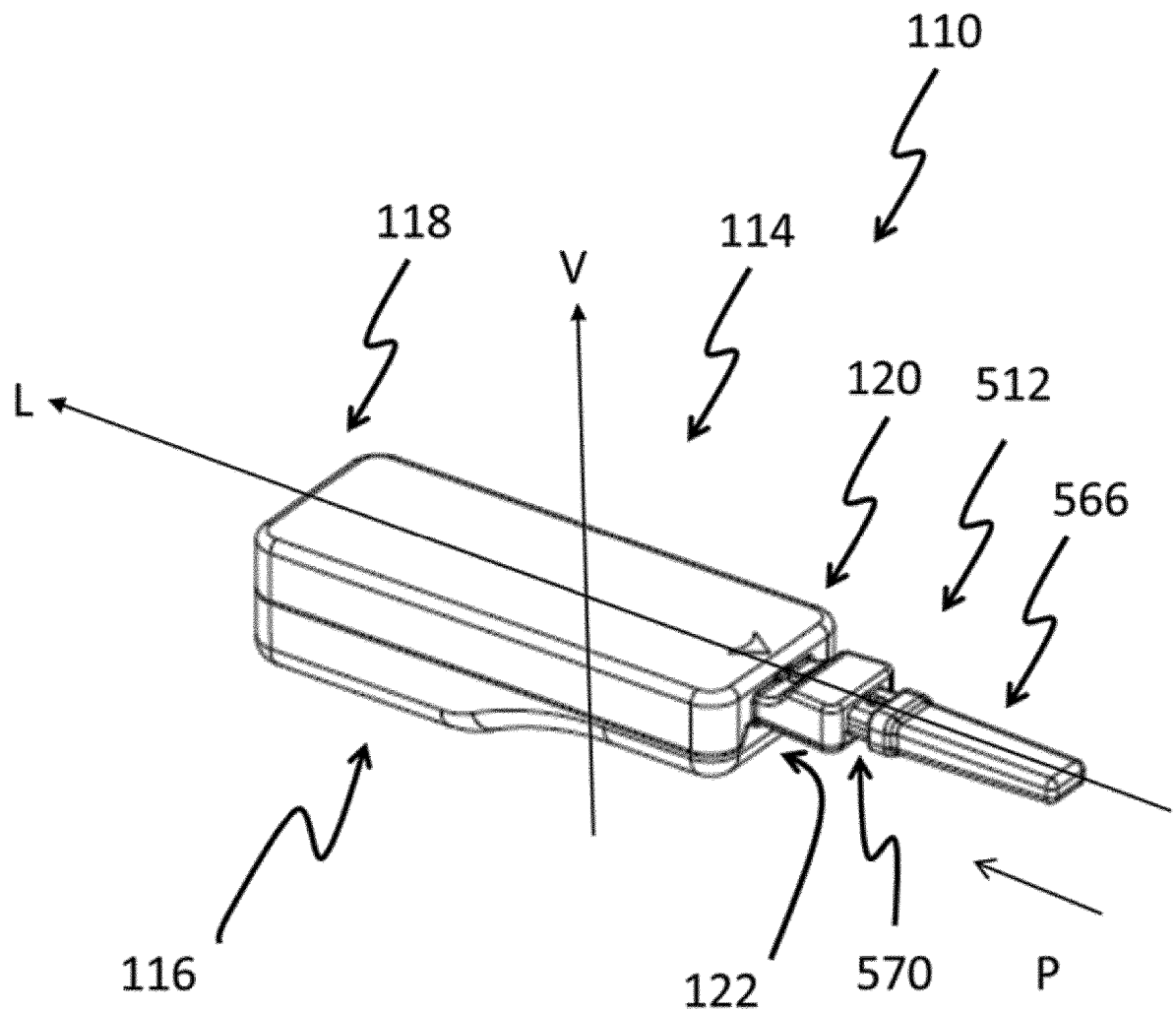
FIG. 4 is a perspective schematic view of a second embodiment of a system for analyzing a biological liquid sample comprising a cartridge for collecting the biological liquid sample and a reader for analyzing the biological liquid sample.
Figure 5:
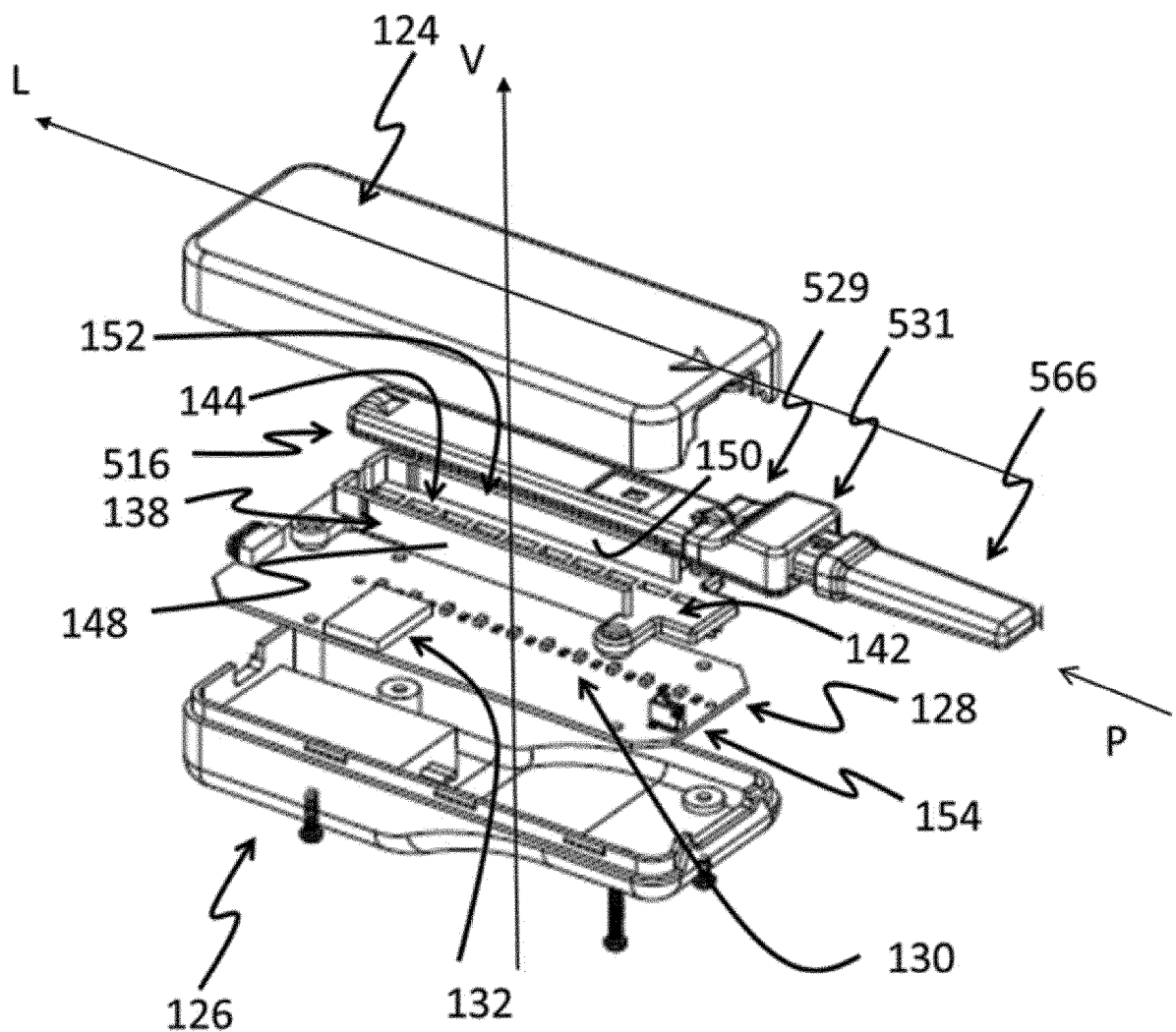
FIG. 5 is a perspective exploded schematic top view of the analysis reader comprising the cartridge for collecting the biological liquid sample according to the second embodiment.
Figure 6:
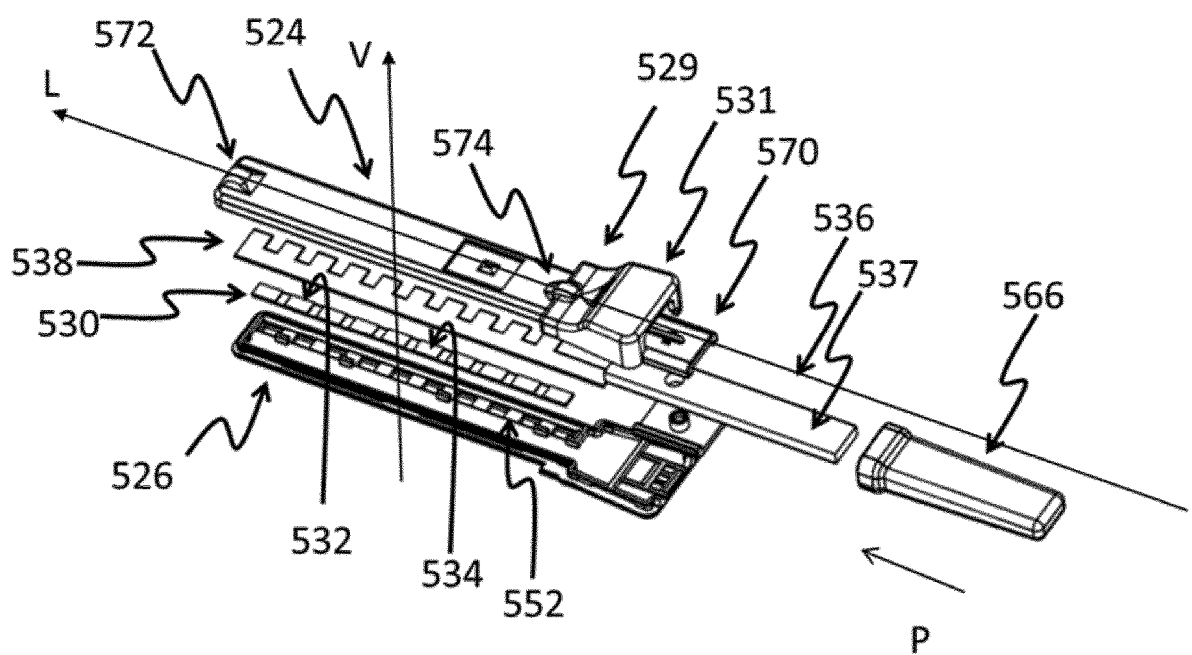
FIG. 6 is a perspective exploded schematic top view of the cartridge for collecting the biological liquid sample according to the second embodiment.

According to FIG. 4, FIG. 5 and FIG. 6, a second embodiment of a system 110 for analyzing a biological liquid sample is represented. The second embodiment, similarly to the first embodiment, comprises a cartridge 512 for collecting a biological liquid sample intended to be inserted into a portable reader 114 for analyzing a biological liquid. The reader 114 comprises a housing 116 of the reader 114 extending generally along the longitudinal axis L between two left and right lateral ends 118, 120. The housing 116 of the reader 114 comprises a lateral access opening 122 intended for an insertion or an extraction of the collection cartridge 512 along the longitudinal axis L. The collection cartridge 512 is configured to be arranged on a cartridge support bottom 142 of a cartridge support element 138 of the reader 114.

Similarly to the first embodiment, the cartridge support element 138 comprises two lateral walls 148, 150 arranged oppositely on either side of the cartridge support bottom 142, each lateral wall 148, 150 extending longitudinally from the lateral access opening 122. The arrangement of the lateral walls 148, 150 on either side of the cartridge support bottom 142 then forms a collection cartridge insertion guide 152.

Similarly to the first embodiment, the reader 114 also comprises an electronic card 128 with printed circuit arranged in the housing bottom 126 of the reader 114. The electronic card 128 with printed circuit comprises a plurality of optical transmitter-receiver assemblies 130, the optical transmitter-receiver assemblies 30 of the plurality of assemblies 30 being arranged one after the other along the longitudinal axis L. The reader 114 comprises an electronic monitoring unit 132, advantageously arranged on the electronic card 128 with printed circuit, and electrically connected to the plurality of optical transmitter-receiver assemblies 130. The reader 114 also comprises a position sensor 154 advantageously arranged on the electronic card 128 with printed circuit.

Also similarly to the first embodiment, the cartridge support bottom 142 comprises a plurality of openings 144, 146 of support bottom 142, each optical transmitter-receiver assembly 130 being arranged facing an opening 144 of the cartridge support bottom 142.

The second embodiment differs in particular from the first embodiment in that the reader 114 and the collection cartridge 512 are configured to cooperate together so as to make reliable the diffusion of a biological liquid sample from a deposition portion 537 of the collection cartridge 512 to the reactive elements 532, 534 of the collection cartridge 512.

To this end, the system 110 comprises a handle 566 configured to be arranged secured to the collection cartridge 512 and allowing exerting a pushing P on the cartridge 512 along the longitudinal axis L when inserting the collection cartridge 512 in translation into the reader 114 through the lateral access opening 122 of the reader 114.

According to the second embodiment, the handle 566 is arranged outside the housing 116 of the reader 114 so as to at least partially cover a portion of an absorbent reservoir band 536 of the collection cartridge 512 extending partially to the outside of the collection cartridge 512. The absorbent reservoir band 536 is configured to comprise the biological liquid deposition portion 537 arranged outside of the collection cartridge 512 and configured to be covered by the handle 566. The handle 566 therefore acts as a cap over the top of the biological liquid deposition portion 537 of the absorbent reservoir band 536.

According to FIG. 6, the absorbent reservoir band 536 is arranged in a movable support 570 configured to slide in a sliding portion 531 of the cartridge housing 516, the sliding portion 531 being arranged at the right end of the collection cartridge 512. The handle 566, arranged around the deposition portion 537 of the absorbent reservoir band 536 is in mechanical connection with the movable support 570, the handle 566 being configured to exert a pushing P in translation on the absorbent reservoir band 536.

According to the second embodiment, the collection cartridge 512 comprises a biological liquid diffusion band 538 extending longitudinally and arranged in the cartridge housing 516 over the top of the plurality of reactive elements 532, 534. The diffusion band 538 is configured to be in direct contact with each reactive element 532, 534 of the collection cartridge 512. Advantageously, the plurality of reactive elements 532, 534 is arranged on the upper face of a strip 530 arranged in the cartridge housing bottom 526, each reactive element 532, 534 being arranged facing an opening 552 of the cartridge housing bottom 526 by transparency through the strip 530.

Figure 7:
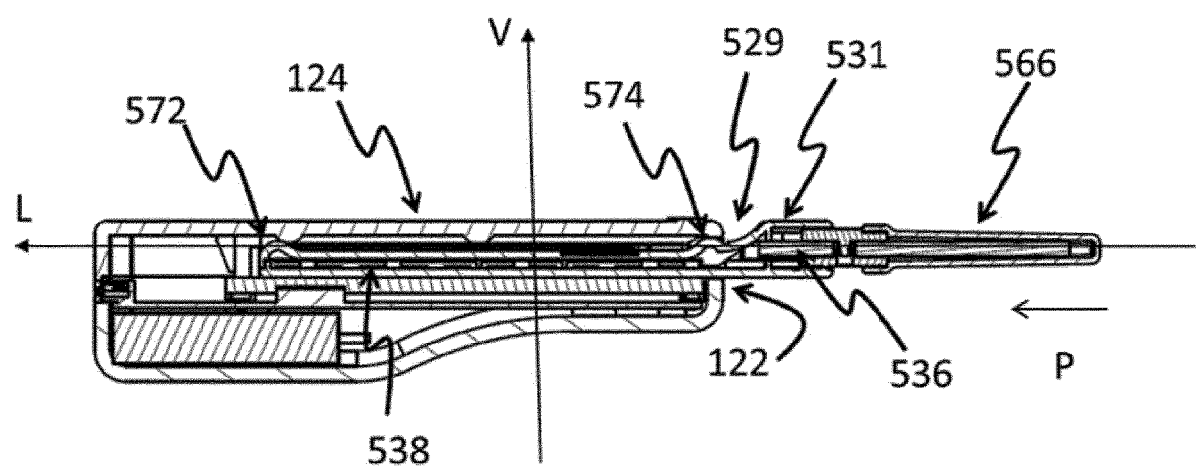
FIG. 7 is a schematic longitudinal sectional view of the analysis reader comprising the cartridge for collecting the biological liquid sample according to the second embodiment of the invention and according to a first positioning of the collection cartridge.

According to FIG. 6 and FIG. 7, and according to the second embodiment, before a maximum insertion of the collection cartridge 512 into the reader 114, that is to say when the collection cartridge 512 is not yet correctly positioned in the reader 114, or even when the reactive elements 532, 534 of the collection cartridge 412 are not all arranged facing an optical transmitter-receiver assembly 130 of reader 114, the absorbent reservoir band 536 is not in contact with the diffusion band 538.

Figure 8:
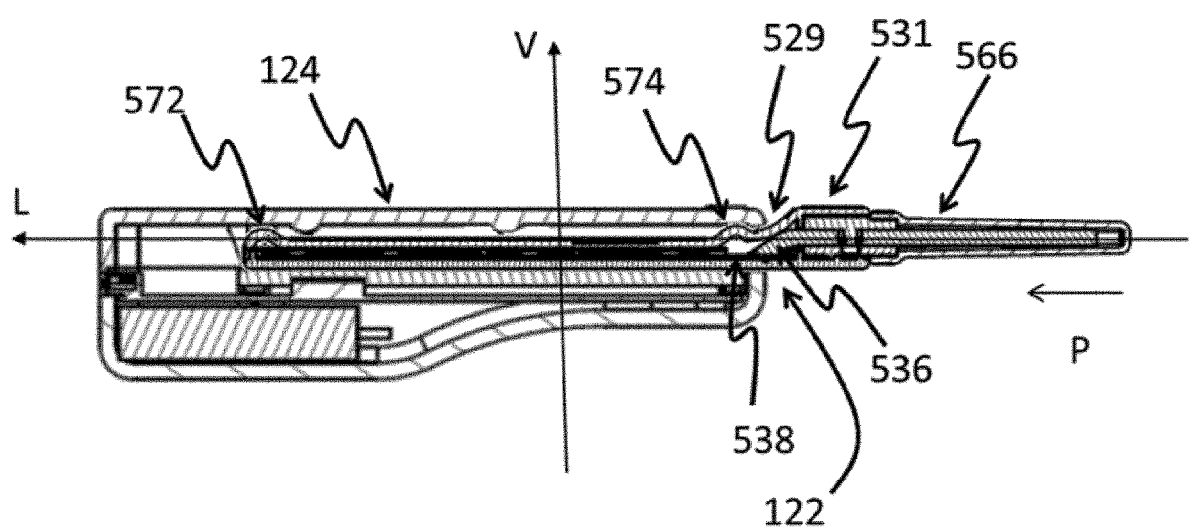
FIG. 8 is a schematic longitudinal sectional view of the analysis reader comprising the cartridge for collecting the biological liquid sample according to the second embodiment of the invention and according to a second positioning of the collection cartridge.

According to FIG. 8, following the insertion in abutment of the collection cartridge 512 into the reader 114, a pushing P along the longitudinal axis L of the handle 566 has the effect of no longer advancing, along the axis longitudinal L, the collection cartridge 512 inserted into the reader 114, but has the effect of pushing the absorbent reservoir band 536 into direct contact with the diffusion band 538. More particularly, the absorbent reservoir band 536 is configured to be pushed by the handle 566 according to a translational movement and guided by the movable support 570 against the inner surface of a transition portion 529 of the housing 516 of the collection cartridge 512, the inner surface of the transition portion 529 having the effect of bending the absorbent reservoir band 536 towards the diffusion band 538 so that contact is made between the two bands 536, 538.

It should be noted that the insertion in abutment of the collection cartridge 512 is effective either when the transition portion 529 abuts against the periphery of the lateral access opening 122 of the reader 114, or alternatively when the left end of the collection cartridge 512, that is to say the end which is opposite the handle 566 abuts in the housing 116 of the reader 114 when it is fully inserted into the reader 114. The solution of a stop obtained by the cooperation between the transition portion 529 of the collection cartridge 512 and the periphery of the lateral access opening 122 of the reader 114 has the advantage of not constraining the design of the reader 114 depending on the length, along the longitudinal axis L of the collection cartridge 512.

According to FIG. 6, FIG. 7 and FIG. 8, in order to improve the reliability of the contact between the diffusion band 538 of the collection cartridge 512 and the reactive elements 532, 534, the housing 516 of the collection cartridge 512 comprises two bosses 572, 574 arranged on the upper wall of the housing 516 of the collection cartridge 512, or else cover 524 of the collection cartridge 512 and protruding outwardly of the housing 516 of the cartridge 512. The cover 524 of the collection cartridge 512 is arranged over the top of the diffusion band 538. According to FIG. 7 and FIG. 8, during the insertion of the collection cartridge 512 into the reader 114, the two bosses 572, 574 are frictionally engaged with the inner face of the cover 124 of the reader 114 so as to exert a downward vertical pressure downwards on the diffusion band 538. The diffusion band 538 thus pressed is maintained in contact with the reactive elements 532, 534 of the collection cartridge.

Figure 9:
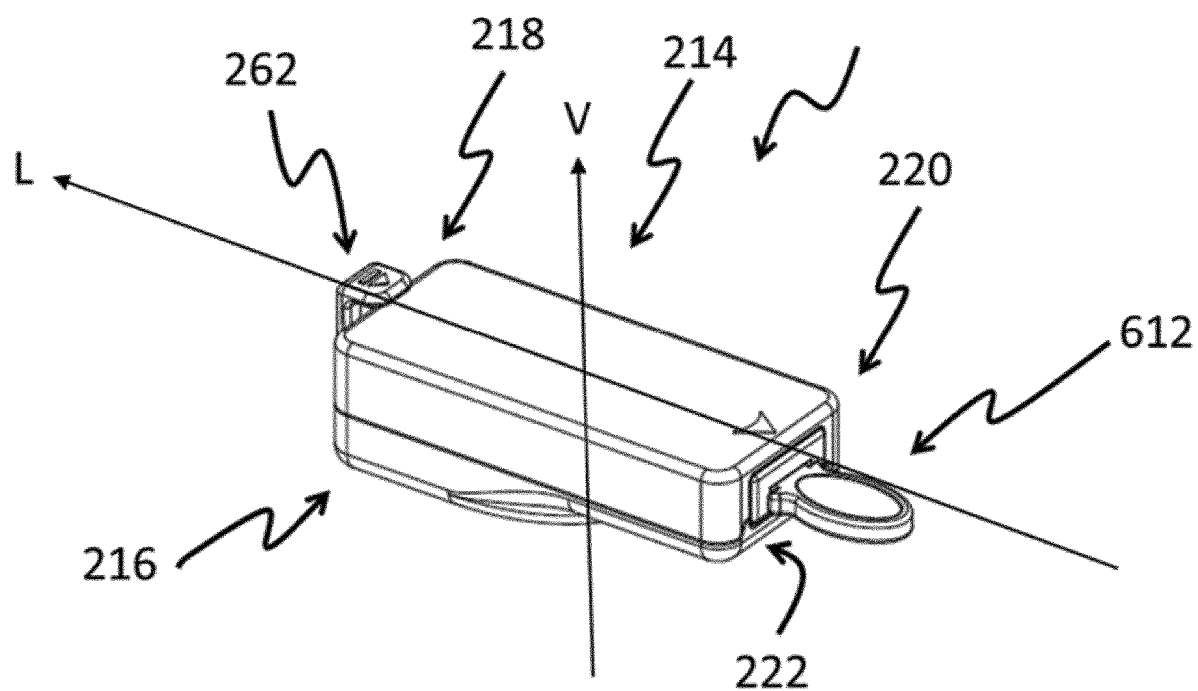
FIG. 9 is a schematic perspective view of a third embodiment of a system for analyzing a biological liquid sample comprising a cartridge for collecting the biological liquid sample and a reader for analyzing the biological liquid sample.
Figure 10:
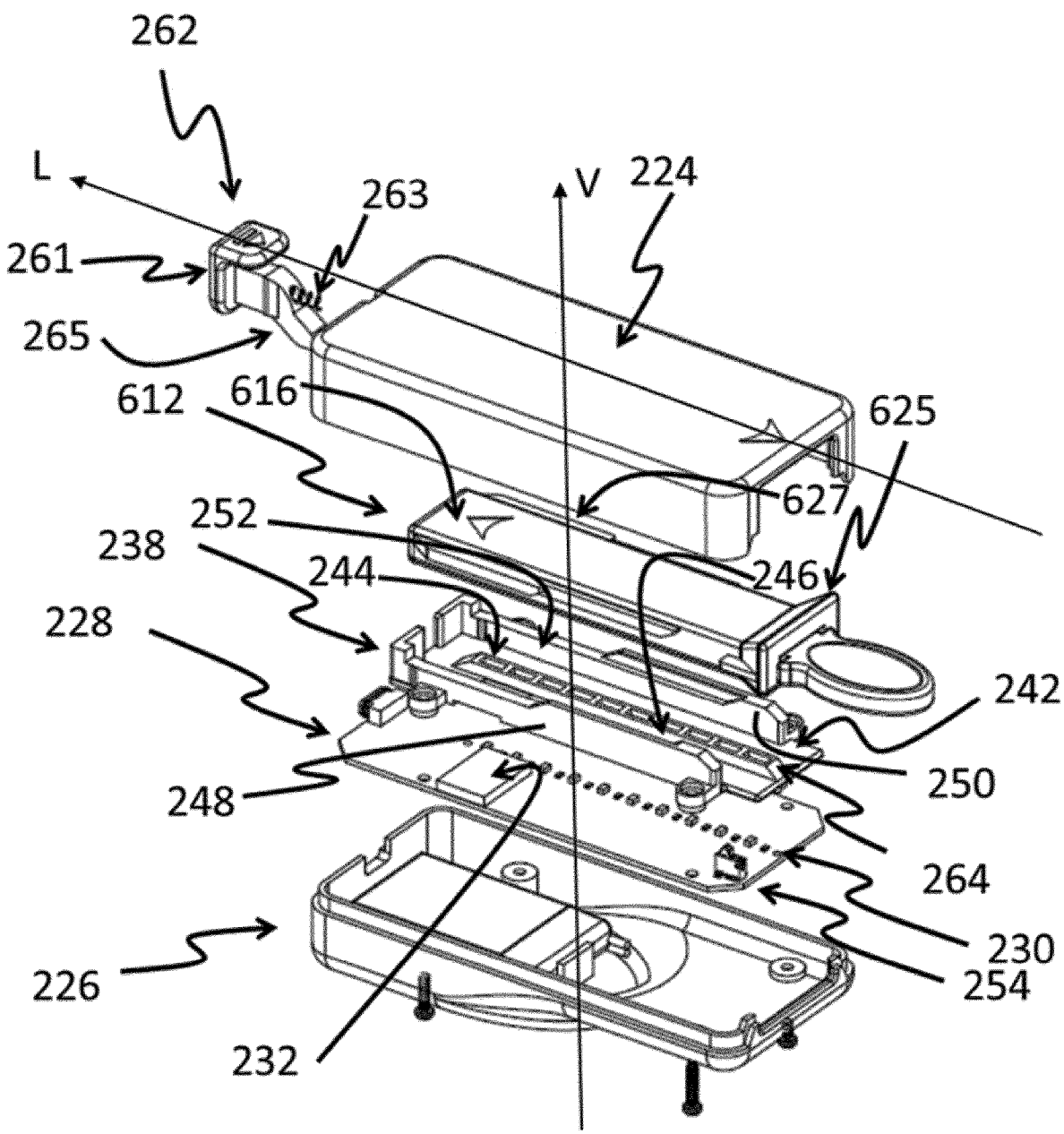
FIG. 10 is a perspective exploded schematic top view of the analysis reader comprising the cartridge for collecting the biological liquid sample according to the third embodiment.
Figure 11:
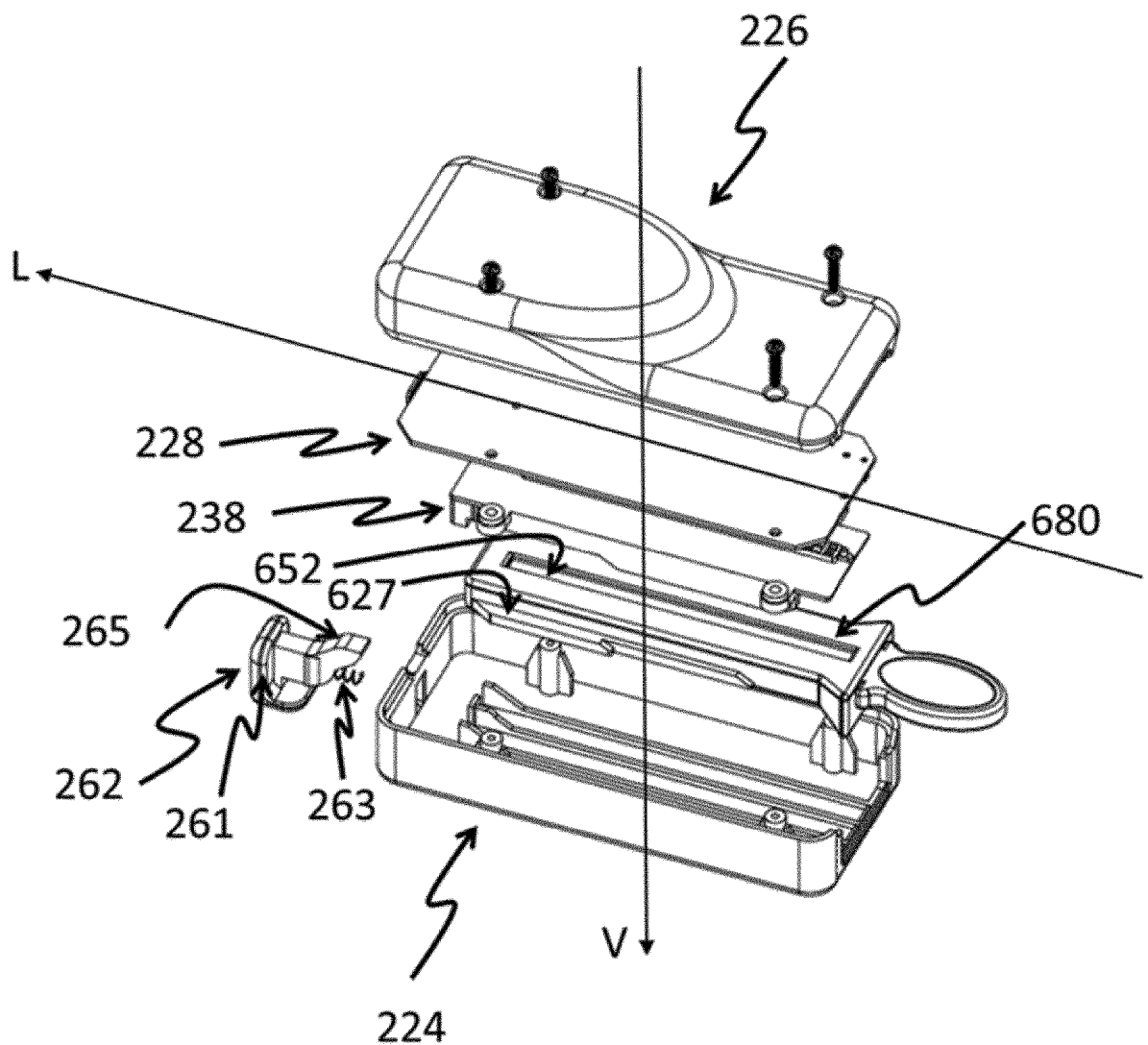
FIG. 11 is a perspective exploded schematic top view of the analysis reader comprising the cartridge for collecting the biological liquid sample according to the third embodiment.

According to FIG. 9, FIG. 10 and FIG. 11, a third embodiment of a system 210 for analyzing a biological liquid sample is represented. The third embodiment, similarly to the first embodiment and the second embodiment, comprises a cartridge 612 for collecting the biological liquid sample intended to be inserted into a portable reader 214 for analyzing the biological liquid. The reader 214 comprises a housing 216 of the reader 214 extending generally along the longitudinal axis L between two left and right lateral ends 218, 220. The housing 216 of the reader 214 comprises a lateral access opening 222 intended for an insertion or an extraction of the collection cartridge 612 along the longitudinal axis L.

Similarly to the first embodiment, the reader 214 also comprises an electronic card 228 with printed circuit arranged in the housing bottom 226 of the reader 214. The electronic card 228 with printed circuit comprises a plurality of optical transmitter-receiver assemblies 230, the optical transmitter-receiver assemblies 230 of the plurality of assemblies 230 being arranged one after the other along the longitudinal axis L. The reader 214 comprises an electronic monitoring unit 232, advantageously arranged on the electronic card 228 with printed circuit, and electrically connected to the plurality of optical transmitter-receiver assemblies 230. The reader 214 also comprises a position sensor 254 advantageously arranged on the electronic card 228 with printed circuit.

Similarly to the first and second embodiment, the reader 214 comprises a cartridge support element 238 comprising two lateral walls 248, 250 oppositely arranged on either side of the cartridge support bottom 242, each lateral wall 248, 250 extending longitudinally from the lateral access opening 222. The arrangement of the lateral walls 248, 250 on either side of the cartridge support bottom 242 then forms a collection cartridge insertion guide 252.

Particularly, as illustrated in FIGS. 10 and 11, the cartridge housing 616 may comprise lateral guide fins 627 configured to be able to slide in grooves arranged on the lateral walls 248, 250 of the insertion guide 252 of the collection cartridge so as to ensure an insertion of the collection cartridge 612 into the reader 214 according to a translational movement.

According to FIG. 10 and FIG. 11, the third embodiment differs from the first and second embodiments in that the cartridge support bottom 242 of the cartridge support element 238 of the reader 214 comprises a protruding portion 264 extending longitudinally on which a plurality of openings 244, 246 of support bottom 242 is arranged.

According to the third embodiment, and similarly to the first and second embodiments, the collection cartridge 612 comprises a plurality of color-changing reactive elements 632, 634 arranged one after the other according to the longitudinal axis L, each reactive element 632, 634 being arranged at the bottom of the cartridge housing 626 and facing an opening 652 of the cartridge housing bottom 626. For the purposes of the third embodiment, the material of the periphery 680 of the opening 652 of the housing bottom 626 of the collection cartridge 612 is a flexible material such as soft plastic.

Figure 12:
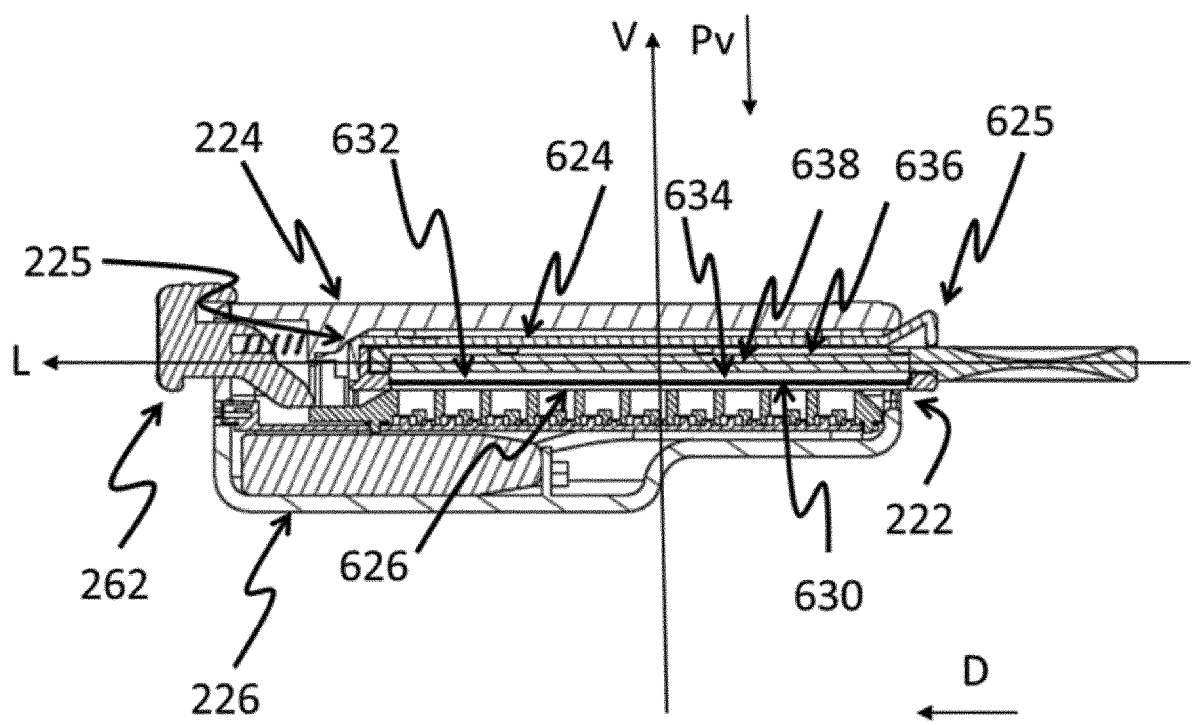
FIG. 12 is a schematic longitudinal sectional view of the analysis reader comprising the cartridge for collecting the biological liquid sample according to the third embodiment of the invention and according to a first positioning of the collection cartridge.

According to FIG. 12, and according to the third embodiment, the collection cartridge 612 comprises a biological liquid diffusion band 638, extending longitudinally, arranged in the cartridge housing 616 over the top of the plurality of reactive elements 632, 634. When the collection cartridge 612 is not yet correctly positioned in the reader 214, the biological liquid diffusion band 638 is not in contact with each reactive element 632, 634.

According to FIG. 12, the system 210 comprises two pushing elements configured to push the collection cartridge 612 according to a vertical pushing Pv towards the cartridge support bottom 242. More particularly, a first pushing element 625 comprises a first bevel-type oblique slope portion arranged on the cartridge cover 624. The first oblique slope portion extends upwardly from the surface of the cartridge cover 624 to the right end of the collection cartridge 612. A second pushing element 225 comprises a second bevel-type oblique slope portion arranged on the inner face of the cover 224 of the reader 214 and directed sloping downwards in the direction D of insertion of the collection cartridge 612.

Figure 13:
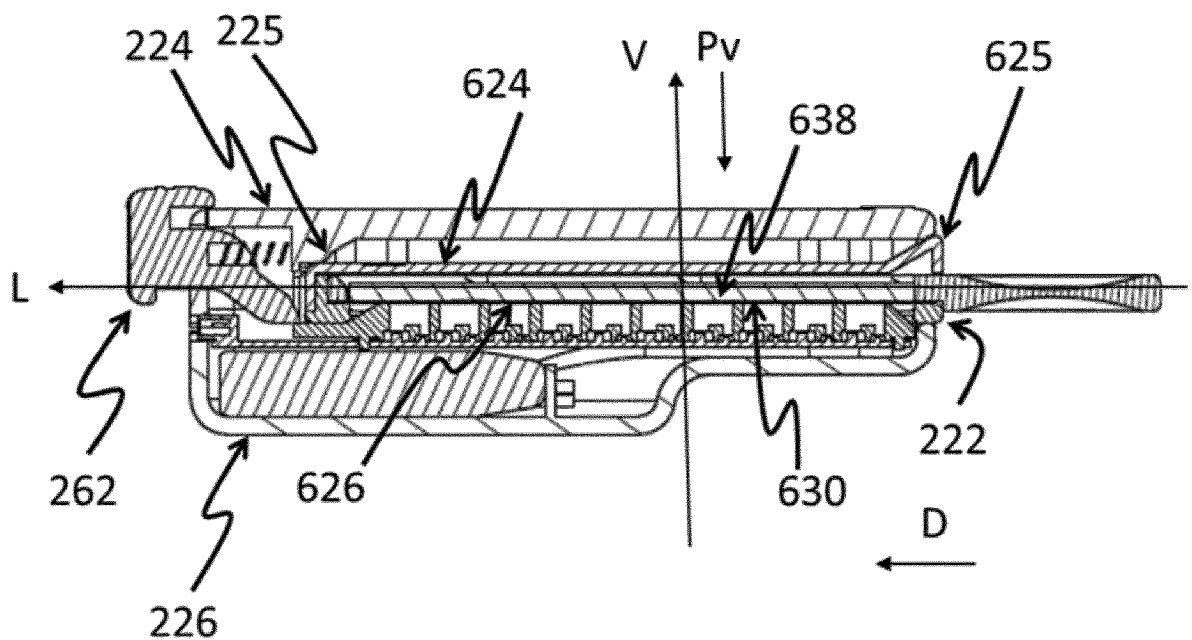
FIG. 13 is a schematic longitudinal sectional view of the analysis reader comprising the cartridge for collecting the biological liquid sample according to the third embodiment of the invention and according to a second positioning of the collection cartridge.

To this end, according to FIG. 13, when inserting the collection cartridge 612 into the reader 214, the first pushing element 625 comes into contact with the lateral access opening 222 of the reader. The second pushing element 225 comes into contact with the left end of the collection cartridge 612. When the collection cartridge 612 is pushed to its maximum insertion position, it is pushed toward the cartridge support bottom 242 such that the periphery 680 of the opening 652 of the housing bottom 626 of the collection cartridge 612 made of flexible material is crashed against the protruding portion 264 of the cartridge support bottom 242. To this end, each reactive element 632, 634 comes into contact with the diffusion band 638. Advantageously, according to this third embodiment, the diffusion band 638 can also act as an absorbent reservoir band 636, such that the diffusion band 638 and the absorbent reservoir band 636 consists of a single absorbent element, for example and without limitation, of the absorbent blotting paper type.

According to FIG. 9, FIG. 10, and FIG. 11, the reader 214 comprises an ejection button 262 configured to eject the collection cartridge 612. The ejection button 262 is arranged on the lateral wall of the left end of the housing 216 of the reader 214, that is to say, on the wall of the reader 214 opposite the lateral access opening 222. The ejection button 262 is arranged through the lateral wall of the left end of housing 216, the ejection button 262 comprising a manual manipulation portion 261 arranged outside the housing 216 of the reader 214. The ejection button 262 also comprises an ejection portion 265 extending from the manipulation portion 261 to the inside of the housing 216 of the reader 214. The ejection portion 265 is configured to slide in translation along the longitudinal axis L over the top of the cartridge support bottom 242 so to be able to hit and eject, through the lateral access opening 222, a collection cartridge 612 having been arranged in the reader 214. To this end and optionally, the ejection button 262 comprises spring means 263 bearing in the housing 216 of the reader 214 and allowing a pushing movement with return to the initial position of the ejection button 262. The advantage of the ejection button 262 is to be able to extract a collection cartridge 612 without having to manipulate it.

Figure 14:
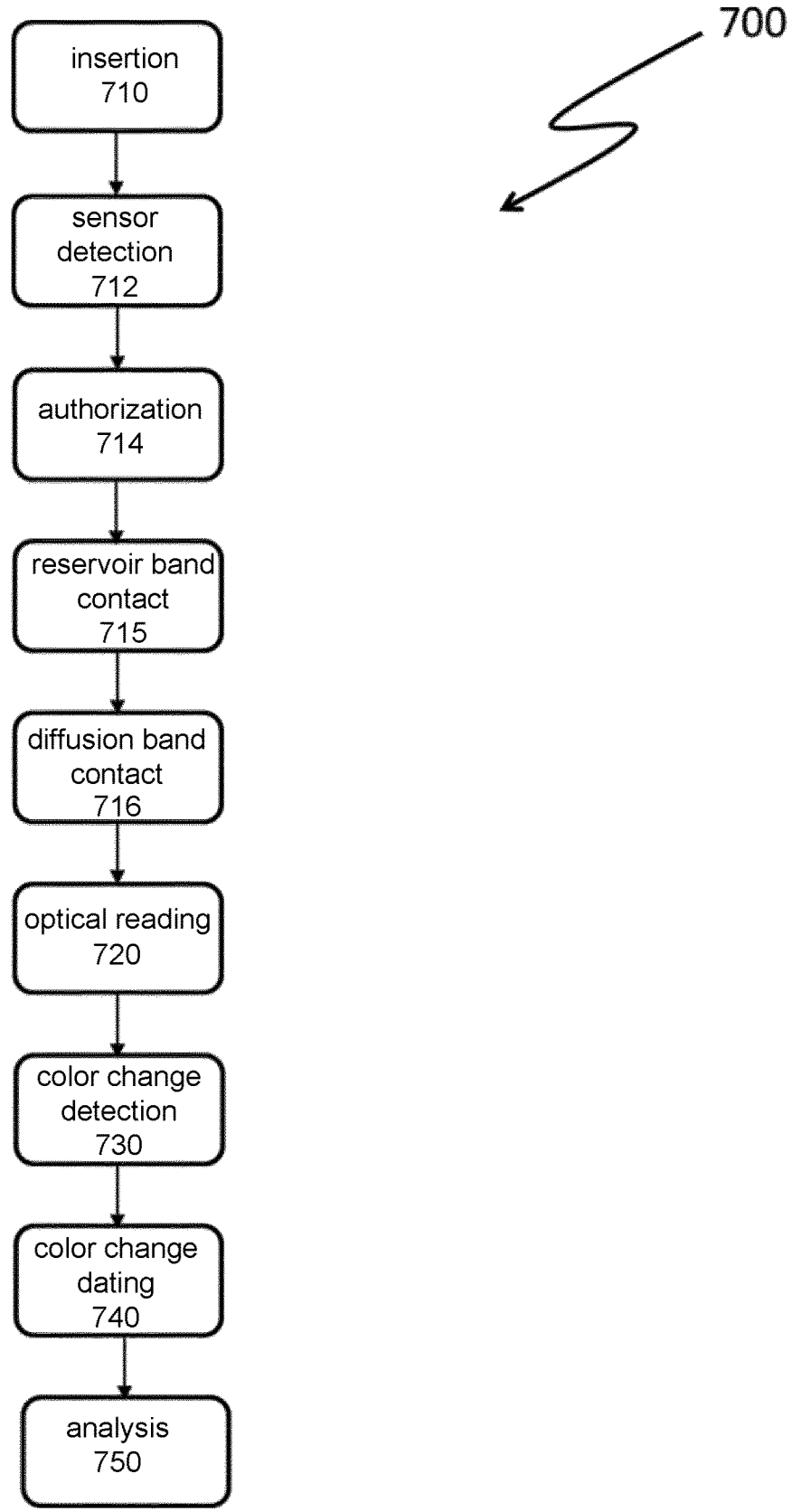
FIG. 14 is a flowchart of a biological liquid sample analysis method implemented by the system for analyzing a biological liquid sample of the embodiments of the preceding figures.

According to FIG. 14, an exemplary method 700 for analyzing a biological liquid sample comprises a plurality of steps. The presented method applies particularly to the systems for analyzing a biological liquid sample of the preceding figures. The method comprises a first step 710 of inserting the collection cartridge 412, 512, 612 into the reader 14, 114, 214. In particular, the insertion is done through a lateral access opening 22, 122, 222 of the reader 14, 114, 214, the lateral access opening 22, 122, 222 allowing the insertion in a longitudinal direction D or the extraction of the collection cartridge 412, 512, 612. A step following the insertion of the collection cartridge 412, 512, 612 consists of a recurrent optical reading 720 of the plurality of reactive elements 432, 532, 632 of the cartridge 412, 512, 612. The term "optical reading" means, in the context of the invention, a reading by light reflection on each reactive element 432, 532, 632 through the openings 452, 552, 652 of the cartridge housing bottom 426, 526, 626 and the strip 430, 530, 630, allowing the detection by the reader 14, 114, 214 of a color change of the reactive elements 432, 532, 632 and therefore allowing the automatic analysis by the reader 14, 114, 214 of the properties of the biological liquid sample to be analyzed.

Following the optical reading step 720 in a recurring manner, the method comprises a step of detecting 730 a first color change of at least one reactive element 432, 532, 632 of the plurality of reactive elements 432, 532, 632, in order to be able to perform a step of dating 740 the first detected color change and also a step of analyzing 750 the biological liquid sample from the cartridge 412, 512, 612 following the detection 130 of a color change of at least one reactive element 432, 532, 632 of the cartridge.

By way of non-limiting example, a color change of a reactive element 432, 532, 632 can be detected by a recurrent calculation performed by the electronic monitoring unit 32, 132, 232 of a ratio of each amount of light of each detected primary color. The reader 14, 114, 214 can then also comprise an electronic memory in which the primary color ratios, associated with each reactive element 432, 532, 632, can be stored so as to be able to determine the presence of a compound of the biological liquid present on each reactive element 432, 532, 632.

Optionally, for a system 10, 110, 210 according to which a position sensor 54, 154, 254 is arranged in the housing 16, 116, 216 of the reader 14, 114, 214, the method may comprise, before the optical reading step 720, a step 712 of detection by a position sensor 54, 154, 254 of the arrangement of each reactive element 432, 532, 632 of the cartridge 412, 512, 612 facing an optical transmitter-receiver assembly 30, 130, 230 of the reader 14, 114, 214, so as also to comprise an additional step of authorizing 714 the step of recurrent optical reading 720 on condition of the detection 712 of the arrangement of each reactive element 432, 532, 632 of the cartridge 412, 512, 612 facing an optical transmitter-receiver assembly 30, 130, 230 of the reader 14, 114, 214.

Optionally, for a system 110, 210 in which a biological liquid diffusion band 538, 638 is arranged over the top of the plurality of reactive elements 532, 632, the method 700 may comprise a direct contact step 716 of the diffusion band 538, 638 on the plurality of reactive elements following the step of inserting the cartridge 512, 612 into the reader 114, 214 by crushing the collection cartridge 512, 612 by the reader 114, 214.

Optionally, for a system 110 according to which the collection cartridge 512 comprises an absorbent reservoir band 536 configured for the deposition of biological liquid, the method 700 may comprise a step 715 of direct contacting of a portion of the absorbent reservoir band 536 on the diffusion band 538 by longitudinal pushing P of the collection cartridge 512 when it is inserted into the reader 114.

It should be noted that the invention is particularly advantageous for the analysis of biological liquid of the urine type. The color-changing reactive elements 432, 532, 632 on contact with urine, arranged in a collection cartridge, according to the invention, can be analyzed by an analysis reader 14, 114, 214 according to the invention, such that the reader can, for example and without limitation, provide information relating to the supervision of the acidity of urine via its hydrogen potential, denoted pH, or even the urinary density and the creatinine concentration thereof. The uric acid concentration is also a possible supervision factor.

It should be noted that in order to have a user-friendly access to the analysis of the reader 14, 114, 214, it is advantageous for the reader 14, 114, 214 to comprise a wired or wireless communication interface allowing communicating with any portable object used as a reading interface for a user of the invention. By way of non-limiting examples, there will be mentioned as portable object, a mobile phone of the smartphone type, or even a computer tablet or a computer.

It should of course be understood that the detailed description of the subject of the invention, given solely by way of illustration, does not in any way constitute a limitation, the technical equivalents also being comprised within the scope of the present invention.

The invention claimed is:

1. A system to analyze a sample of a biological liquid comprising:
   a portable reader to analyze the sample of the biological liquid comprising:
      a reader housing of the portable reader extending along a longitudinal axis between two lateral ends, the reader housing comprising: a lateral access opening for inserting or extracting a collection cartridge along the longitudinal axis, a lower portion of the reader housing comprising a housing bottom of the portable reader, and a cover of the portable reader to close the reader housing;
      an electronic card with printed circuit arranged in the housing bottom of the portable reader;
      a plurality of optical transmitter-receiver assemblies arranged on an upper face of the electronic card, the plurality of optical transmitter-receiver assemblies being arranged one after the other along the longitudinal axis;
      a cartridge support element extending longitudinally comprising a cartridge support bottom extending longitudinally, and the cartridge support bottom arranged facing the upper face of the electronic card, the cartridge support bottom comprising a protruding portion, extending along the longitudinal axis, on which a plurality of openings of the cartridge support bottom is arranged, each optical transmitter-receiver assembly being arranged facing one of the plurality of openings of the cartridge support bottom; and
      an electronic monitoring unit electrically connected to the plurality of optical transmitter-receiver assemblies, the electronic monitoring unit controls said each optical transmitter-receiver assembly in a mode of emitting light and receiving a reflected light so as to perform an optical reading to analyze the biological liquid;
   the collection cartridge to collect the sample of the biological liquid, the collection cartridge being arranged to bear on the cartridge support bottom of the portable reader, the collection cartridge comprising:
      a cartridge housing extending longitudinally between two lateral ends and comprising a cartridge housing bottom comprising an opening and a flexible portion forming a periphery of the opening of the cartridge housing bottom;
      a plurality of color-changing reactive elements arranged one after the other along the longitudinal axis, each reactive element being arranged in the cartridge housing bottom and facing the opening of the cartridge housing bottom;
      a biological liquid diffusion band, extending longitudinally, arranged in the cartridge housing over a top of the plurality of color-changing reactive elements, the biological diffusion band being in direct contact with said each reactive element only when the collection cartridge is correctly positioned in the portable reader; and
      a cartridge cover arranged over a top of the biological diffusion band;
   the electronic monitoring unit analyzes the sample of the biological liquid by detecting a color change of said each reactive element following an optical reading; and
   at least one pushing element cooperating with the cartridge cover to:
      push the collection cartridge in a direction of the cartridge support bottom; and
      crush the flexible portion of the cartridge housing bottom against the protruding portion of the cartridge support bottom when the collection cartridge is inserted into the portable reader such that said each reactive element comes into contact with the diffusion band.

2. The system of claim 1, further comprising a position sensor arranged in the reader housing and electrically connected to the monitoring unit, the position sensor:
   detects that said each reactive element of the collection cartridge is arranged facing the optical transmitter-receiver assemblies of the portable reader; and
   sends a control signal, to the electronic monitoring unit, for optical reading of said each reactive element in a recurrent manner following the detection of an arrangement facing said each reactive element with the optical transmitter-receiver assemblies.

3. The system of claim 1, wherein the cartridge support element comprises two lateral walls extending longitudinally from the lateral access opening and arranged on either side of the cartridge support bottom forming a guide for inserting the collection cartridge.

4. A method for analyzing a sample of a biological liquid, comprising:
   implementing the system to analyze the sample of the biological liquid of claim 1, the collection cartridge comprising the biological liquid diffusion band arranged over the top of the plurality of reactive elements;
   inserting the collection cartridge into the portable reader;
   directly contacting the biological liquid diffusion band on the plurality of reactive elements by crushing the collection cartridge inserted therein by the portable reader
   recurrent optical reading of the plurality of reactive elements of the collection cartridge following the insertion of the collection cartridge;
   detecting a color change of at least one reactive element of the plurality of reactive elements following the recurrent optical reading of the plurality of reactive elements;
   dating the color change detected; and
   analyzing the sample of the biological liquid of the collection cartridge following a detection of the color change of said at least one reactive element of the collection cartridge.

5. The method of claim 4, wherein the portable reader comprises a position sensor arranged in the reader housing, the method comprising, prior to the recurrent optical reading:
   detecting, by the position sensor, an arrangement of said each reactive element of the collection cartridge facing the optical transmitter-receiver assemblies of the portable reader; and
   authorizing the recurrent optical reading in response to a detection of the arrangement of said each reactive element of the collection cartridge facing the optical transmitter-receiver assemblies of the portable reader.

6. The method of claim 4, wherein the collection cartridge comprises an absorbent reservoir band for depositing the biological liquid, the method comprising directly contacting a portion of the absorbent reservoir band with the diffusion band by longitudinally pushing the collection cartridge inserted into the portable reader.

\* \* \* \* \*